(12) United States Patent
Fischer et al.

(10) Patent No.: US 8,552,158 B2
(45) Date of Patent: Oct. 8, 2013

(54) METHOD FOR THE PRODUCTION OF INSULIN-LIKE GROWTH FACTOR-1

(75) Inventors: Stephan Fischer, Polling (DE);
Friederike Hesse, Munich (DE);
Hendrik Knoetgen, Penzberg (DE);
Kurt Lang, Penzberg (DE); Joerg Thomas Regula, Munich (DE);
Christian Schantz, Munich (DE);
Andreas Schaubmar, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 279 days.

(21) Appl. No.: 12/438,154

(22) PCT Filed: Aug. 29, 2007

(86) PCT No.: PCT/EP2007/007539
§ 371 (c)(1),
(2), (4) Date: Oct. 30, 2009

(87) PCT Pub. No.: WO2008/025527
PCT Pub. Date: Mar. 6, 2008

(65) Prior Publication Data
US 2010/0121036 A1 May 13, 2010

(30) Foreign Application Priority Data
Aug. 31, 2006 (EP) ................................. 06018171

(51) Int. Cl.
*A61K 38/30* (2006.01)
*C12P 21/06* (2006.01)
*C12N 15/18* (2006.01)

(52) U.S. Cl.
USPC ......... 530/399; 435/69.1; 435/68.1; 435/70.1

(58) Field of Classification Search
None
See application file for complete search history.

(56) References Cited

U.S. PATENT DOCUMENTS

| | | | |
|---|---|---|---|
| 4,904,584 A | 2/1990 | Shaw | |
| 5,158,875 A | 10/1992 | Miller et al. | |
| 5,427,927 A | 6/1995 | Meyer et al. | |
| 5,672,662 A | 9/1997 | Harris et al. | |
| 5,681,814 A | 10/1997 | Clark et al. | |
| 5,714,460 A | 2/1998 | Gluckman et al. | |
| 5,861,373 A | 1/1999 | Gluckman et al. | |
| 5,932,462 A | 8/1999 | Harris et al. | |
| 6,403,764 B1 | 6/2002 | Dubaquie et al. | |
| 6,506,874 B1 | 1/2003 | Dubaquie et al. | |
| 6,509,443 B1 | 1/2003 | Dubaquie et al. | |
| 6,559,122 B1 | 5/2003 | Oeswein et al. | |
| 6,623,950 B1 | 9/2003 | von der Osten et al. | |
| 7,431,921 B2 | 10/2008 | Rasmussen et al. | |
| 7,662,933 B2 | 2/2010 | Kinstler et al. | |
| 2002/0192718 A1 | 12/2002 | Tom-moy et al. | |
| 2003/0109427 A1 | 6/2003 | Shirley et al. | |
| 2003/0204864 A1 | 10/2003 | Daniell | |
| 2004/0014156 A1 | 1/2004 | Roffler et al. | |
| 2004/0014652 A1 | 1/2004 | Trouet et al. | |
| 2004/0053370 A1 | 3/2004 | Glaesner et al. | |
| 2004/0136952 A1 | 7/2004 | Bhaskaran et al. | |
| 2006/0074011 A1 | 4/2006 | Shirley et al. | |
| 2006/0166328 A1* | 7/2006 | Glass et al. ................... 435/69.4 |
| 2009/0253628 A1 | 10/2009 | Noltmann et al. | |

FOREIGN PATENT DOCUMENTS

| | | |
|---|---|---|
| DE | 3924705 | 1/1991 |
| EP | 0123228 | 10/1984 |
| EP | 0128733 | 12/1984 |
| EP | 400472 | 12/1990 |
| EP | 473084 | 3/1992 |
| EP | 597033 | 5/1994 |
| EP | 0972838 | 1/2000 |
| EP | 1674113 | 6/2006 |
| JP | 5-501360 | 3/1993 |
| JP | 2004-528014 | 9/2004 |
| WO | 91/02807 | 3/1991 |
| WO | WO 91/02807 | 3/1991 |
| WO | 91/11520 | 8/1991 |
| WO | WO 91/11520 | 8/1991 |
| WO | 93/02695 | 2/1993 |
| WO | 94/12219 | 6/1994 |
| WO | 95/32003 | 11/1995 |
| WO | 99/46597 | 9/1999 |
| WO | 99/55362 | 11/1999 |
| WO | 99/62536 | 12/1999 |
| WO | 01/88149 | 11/2001 |
| WO | 01/91798 | 12/2001 |
| WO | 02/32449 | 4/2002 |
| WO | 02/094853 | 11/2002 |
| WO | 2004/060300 | 7/2004 |
| WO | 2006/066891 | 6/2006 |
| WO | 2006/074390 | 7/2006 |
| WO | WO 2006/074390 | 7/2006 |
| WO | 2008/025528 | 3/2008 |
| WO | WO 2008/025527 | 3/2008 |
| WO | 2009/121759 | 10/2009 |

OTHER PUBLICATIONS

Database Geneseq—XP002416949, Jun. 17, 2004.
Database Geneseq—XP002416950, Jun. 17, 2004.
Database Geneseq—XP002416951, Nov. 4, 2004.
Database Geneseq—XP002416952, Nov. 4, 2004.
Pohlner et al., *Bio/Technology*, 10:799-804 (1992).

(Continued)

*Primary Examiner* — Gyan Chandra

(57) ABSTRACT

Method for the production of IGF-I, characterized by cultivating a prokaryotic host cell comprising an expression vector containing a nucleic acid encoding a fusion protein comprising said IGF-I N-terminally linked to the C-terminus of a propeptide, whereby said propeptide ends C-terminally with amino acids -Y-Pro, wherein Y is selected from the group consisting of Pro, Pro-Ala, Pro-Gly, Pro-Thr, Ala-Pro, Gly-Pro, Thr-Pro, Arg-Pro, or Pro-Arg-Pro, recovering and cleaving said fusion protein with IgA protease, and recovering said IGF-I. IGF-I is useful for the treatment of neurodegenerative disorders like Alzheimer's Disease.

4 Claims, No Drawings

(56) References Cited

OTHER PUBLICATIONS (*Translation of Japanese Office Action* in Corres. Appl 2009-525970 Sep. 27, 2011).
Pohlner, J. et al., *Gene* 130(1):121-126 (1993).
Nishikawa, S. et al., *Protein Engineering* 1(6):487-492 (1987).
Forsberg, G. et al., *Journal Protein Chem.* 11(2):201-211 (1992).
(Database Geneseq—XP002416949 Jun 17, 2004).
Pohlner et al., Bio/Technology 10:799-804 (1992).
(Database Geneseq—XP002416951 Nov 4, 2004).
(International Search Report Nov 26, 2007).
(Database Geneseq—XP002416950 Jun 17, 2004).
(Database Geneseq—XP002416952 Nov 4, 2004).
Veronese, Biomaterials 22:405-417 (2001).
Veronese et al., J. Bioactive and Compatible Polymers 12:196-207 (1997).
Foser et al., Pharmacogenomic Journal 3:312-319 (2003).
(International Search Report Aug 8, 2005).
Carro et al., Nat. Med. 8:1390-1397 (2002).
Baljit Singh et al., The Journal of Biological Chemistry 270(46):27481-27488 (1995).
Sandberg et al., "Brain Res. Mol. Brain Res." 12:275-277 (1992).
Philippe et al., Journal of Immunological Methods 180(2):247-257 (1995).
Dore et al., Proc. Natl. Acad. Sci. USA 94:4772-4777 (1997).
Kinstler et al., Drug Deliv. Rev. 54:477-485 (2002).
Uthne et al., "J. Clin. Endocrinol. Metab." 39:548-554 (1974).
Pagter-Holthuizen et al., "FEBS Lett." 195:179-184 (1986).
23907 US2 (Final Office Action in U.S. Appl. No. 12/767,829 Feb 29, 2012).
Carro et al., European J. Pharmacology 490(1-3):127-133 (2004).
Brzozowski et al., Biochem. 41:9389-9397 (2002).
Dore et al., Ann. NY Acad. Sci. 890:356-364 (1999).
23907 US2 (Office Action in U.S. Appl. No. 12/767,829 Jul 20, 2011).
(International Search Report for PCT/ep2010/070174 Mar 8, 2011).
Esposito et al., Advanced Drug Delivery Review 55:1279-1291 (2003).
Kohyo, Japanese Laid-open Patent Publication No. Hei 10-500693 (1998).
March, Advanced Organiz Chemistry:375-376 (1977).
Greenwald, J. Controlled Release 74:159-171 (2001).
Monfardini et al., Bioconjugate Chem. 6:62-69 (1995).
Park et al., Pharmaceutical Research 19:845-851 (2002).
(International Search Report for PCT/EP2009/002319 Jun 23, 2009).
Hermanson, Bioconjugate Techniques, Academic Press, San Diego:147-148 (1996).
English Translation of Japanese Office Action in Corres. Appl. No. 2007-547330 dated May 24, 2011.
Duncan et al., Anal. Biochem. 132:68-73 (1983).
Lebouc et al., FEBS Lett. 196:108-112 (1986).
(International Search Report Feb 5, 2007).
(Translation of Japanese Office Action in Corresponding Appl. 2009-525971 Sep. 2, 2011).
Morpurgo et al., J. Bioconjugate Chem. 7:363-368 (1996).
Pohlner et al., Nature 325:458-462 (1987).
Tanner et al., "Acta Endocrinol." 84:681-696 (1977).
(Office Action in corresponding Japanese Patent App. 2007-547330 Jun 29, 2010).
Richards et al., J. Neuroscience 23:8989-9003 (2003).
Grassetti et al., Archives of Biochemistry and Biophysics 119:41-49 (1967).
Robinson et al., Biochem. 43:11533-11545 (2004).
Kohyo, Japanese Laid-open Patent Publication No. Hei 8-506095 (1996).
Kim et al., Biomaterials 23:2311-2317 (2002).
Kiefer et al., Biochem. Biophys. Res. Commun. 176:219-225 (1991).
Shimasaki et al., Mol. Endocrinol.:1451-1458 (1990).
Steenbergh et al., "Biochem. Biophys. Res. Commun." 175:507-514 (1991).
Harris et al., Clin. Pharmacokinetic 40:539-551 (2001).

\* cited by examiner

METHOD FOR THE PRODUCTION OF INSULIN-LIKE GROWTH FACTOR-1

This application is the national phase application of PCT/EP2007/007539 which claims the benefit of European Patent Application No. 06018171.6, filed Aug. 31, 2006. The entire contents of the above-identified applications are hereby incorporated by reference.

SEQUENCE LISTING

The instant application contains a Sequence Listing which has been submitted in ASCII format via EFS-Web and is hereby incorporated by reference in its entirety. Said ASCII copy, created on Mar. 6, 2012, is named 23908.txt and is 18,619 bytes in size.

This invention relates to a method for the production of insulin-like growth factor-I (IGF-I), pharmaceutical compositions, and methods of use.

BACKGROUND OF THE INVENTION

Human insulin-like growth factor I (IGF-I) is a circulating hormone structurally related to insulin. IGF-I is traditionally considered the major mediator of the actions of growth hormone on peripheral tissues. Naturally-occurring IGF-I consists of 70 amino acids and is also named somatomedin C and defined by SwissProt No. P01343. Use, activity and production are mentioned in, e.g., le Bouc, Y., et al., FEBS Lett. 196 (1986) 108-112; de Pagter-Holthuizen, P., et al., FEBS Lett. 195 (1986) 179-184; Sandberg Nordqvist, A. C., et al., Brain Res. Mol. Brain Res. 12 (1992) 275-277; Steenbergh, P. H., et al., Biochem. Biophys. Res. Commun. 175 (1991) 507-514; Tanner, J. M., et al., Acta Endocrinol. (Copenh.) 84 (1977) 681-696; Uthne, K., et al., J. Clin. Endocrinol. Metab. 39 (1974) 548-554; EP 0 123 228; EP 0 128 733; U.S. Pat. No. 5,861,373; U.S. Pat. No. 5,714,460; EP 0 597 033; WO 02/32449; WO 93/02695.

The regulation of IGF-I function is quite complex. In the circulation, only 0.2% of IGF-I exists in the free form whereas the majority is bound to IGF-binding proteins (IGFBP's), which have very high affinities to IGF's and modulate IGF-I function. The factor can be locally liberated by mechanisms releasing IGF-I such as proteolysis of IGFBPs by proteases.

IGF-I plays a paracrine role in the developing and mature brain (Werther, G. A., et al., Mol. Endocrinol. 4 (1990) 773-778). In vitro studies indicate that IGF-I is a potent non-selective trophic agent for several types of neurons in the CNS (Knusel, B., et al., J. Neurosci. 10 (1990) 558-570; Svrzic, D., and Schubert, D., Biochem. Biophys. Res. Commun. 172 (1990) 54-60), including dopaminergic neurons (Knusel, B., et al., J. Neurosci. 10 (1990) 558-570) and oligodendrocytes (McMorris, F. A., and Dubois-Dalcq, M., J. Neurosci. Res. 21 (1988) 199-209; McMorris, F. A., et al., Proc. Natl. Acad. Sci. USA 83 (1986) 822-826; Mozell, R. L., and McMorris, F. A., J. Neurosci. Res. 30 (1991) 382-390)). U.S. Pat. No. 5,093,317 mentions that the survival of cholinergic neuronal cells is enhanced by administration of IGF-I. It is further known that IGF-I stimulates peripheral nerve regeneration (Kanje, M., et al., Brain Res. 486 (1989) 396-398) and enhance ornithine decarboxylase activity U.S. Pat. No. 5,093,317). U.S. Pat. No. 5,861,373 and WO 93/02695 mention a method of treating injuries to or diseases of the central nervous system that predominantly affects glia and/or non-cholinergic neuronal cells by increasing the active concentration(s) of IGF-I and/or analogues thereof in the central nervous system of the patient.

WO 02/32449 is directed to methods for reducing or preventing ischemic damage in the central nervous system of a mammal by administering to the nasal cavity of the mammal a pharmaceutical composition comprising a therapeutically effective amount of IGF-I or biologically active thereof. IGF-I is absorbed through the nasal cavity and transported into the central nervous system of the mammal in an amount effective to reduce or prevent ischemic damage associated with an ischemic event. EP 0874641 claims the use of an IGF-I or an IGF-II for the manufacture of a medicament for treating or preventing neuronal damage in the central nervous system, due to AIDS-related dementia, Alzheimer's disease (AD), Parkinson's Disease, Pick's Disease, Huntington's Disease, hepatic encephalopathy, cortical-basal ganglionic syndromes, progressive dementia, familial dementia with spastic parapavresis, progressive supranuclear palsy, multiple sclerosis, cerebral sclerosis of Schilder or acute necrotizing hemorrhagic encephalomyelitis, wherein the medicament is in a form for parenteral administration of an effective amount of said IGF outside the blood-brain barrier or blood-spinal cord barrier.

Reduction of brain and serum levels of free IGF-I has been related to the pathogenesis of sporadic and familial forms of AD. Furthermore, IGF-I protects neurons against Aβ-induced neurotoxicity (Niikura, T., et al., J. Neurosci. 21 (2001) 1902-1910; Dore, S., et al., Proc. Natl. Acad. Sci. USA 94 (1997) 4772-4777; Dore, S., et al., Ann. NY Acad. Sci. 890 (1999) 356-364). Recently, it was shown that peripherally administered IGF-I is capable of reducing brain Aβ levels in rats and mice (Carro, E., et al., Nat. Med. 8 (2002) 1390-1397). Furthermore, the study demonstrated that in a transgenic AD mouse model prolonged IGF-I treatment significantly reduced brain amyloid plaque load. These data strongly support the idea that IGF-I is able to reduce brain AB levels and plaque-associated brain dementia by clearing Aβ from the brain.

The recognition site of the IgA Protease is described as Yaa-Pro.!.Xaa-Pro. Yaa stands for Pro (or rarely for Pro in combination with Ala, Gly or Thr: Pro-Ala, Pro-Gly, or Pro-Thr. Xaa stands for Thr, Ser or Ala (Pohlner, J. et al., Bio/Technology 10 (1992) 799-804; Pohlner, J. et al., Nature 325 (1987) 458-462 and U.S. Pat. No. 5,427,927). Naturally cleavage sites have been identified by Wood, S. G. and Burton, J., Infect Immun. 59 (1991) 1818-1822. Synthetic peptide substrates for the immunoglobulin A1 protease from *Neisseria gonorrhoeae* (type 2) are the autoproteolytic sites Lys-Pro-Ala-Pro.!.Ser-Pro (SEQ ID NO: 22), Val-Ala-Pro-Pro.!.Ser-Pro (SEQ ID NO: 23), Pro-Arg-Pro-Pro.!.Ala-Pro (SEQ ID NO: 24), Pro-Arg-Pro-Pro.!.Ser-Pro (SEQ ID NO: 25), Pro-Arg-Pro-Pro.!.Thr-Pro (SEQ ID NO: 26) and the IgA1 Cleavage Sites Pro-Pro-Thr-Pro.!.Ser-Pro (SEQ ID NO: 27) and Ser-Thr-Pro-Pro.!.Thr-Pro (SEQ ID NO: 28).

WO 2006/066891 discloses conjugates consisting of an insulin-like growth factor-1 (IGF-I) and one or two poly (ethylene glycol) group(s), characterized in that said IGF-I has an amino acid alteration at up to three amino acid positions 27, 37, 65, 68 of the wild-type IGF-I amino acid sequence so that one or two of said amino acids is/are lysine and amino acid 27 is a polar amino acid but not lysine, is conjugated via the primary amino group(s) of said lysine(s) and said poly(ethylene glycol) group(s) have an overall molecular weight of from 20 to 100 kDa. Such conjugates are useful for the treatment of neurodegenerative disorders like Alzheimer's Disease.

WO2006/074390 refers to IGF-I variants and fusion proteins comprising IGF-I variants and certain fusion components. WO 2006/074390 refers to certain IGF-I variants.

Methods for the recombinant production of IGF-I via a fusion protein are known, e.g., from EP0155655 and U.S. Pat. No. 5,158,875. However microheterogenity of recombinantly produced IGGF-I is often found (Forsberg, G. et. al., Biochem. J. 271 (1990) 357-363).

SUMMARY OF THE INVENTION

The invention provides a method for the recombinant production of IGF-I without N-terminal attached methionine in prokaryotes with high purity and yield. The invention comprises a method for the production of IGF-I, said method comprising:

a) cultivating a prokaryotic host cell comprising an expression vector containing a nucleic acid encoding a fusion protein comprising said IGF-I N-terminally linked to the C-terminus of a propeptide, whereby said propeptide ends C-terminally with amino acids -Y-Pro, wherein Y is selected from the group consisting of Pro, Pro-Ala, Pro-Gly, Pro-Thr, Ala-Pro, Gly-Pro, Thr-Pro, Arg- Pro, and Pro-Arg-Pro, and b) recovering and cleaving said fusion protein with IgA protease to recover said IGF-I.

The recovered IGF-I comprises no methionine residue attached at the N-terminus.

In a preferred embodiment of the invention, the a propeptide is selected from the group consisting of peptides shown in SEQ ID NO: 2-5.

A further embodiment of the invention is a fusion protein comprising said IGF-I N-terminally linked to the C-terminus of a propeptide, wherein said propeptide ends C-terminally with amino acids -Y-Pro, wherein Y is selected from the group consisting of Pro, Pro-Ala, Pro-Gly, Pro-Thr, Ala-Pro, Gly-Pro, Thr-Pro, Arg-Pro, and Pro-Arg-Pro. Due to the -Y- Pro sequence the propeptide can be separated by IgA protease treatment from said IGF-I.

Preferably the fusion protein according to the invention has the following amino acid sequence: Met-$X_1$-His$_n$-$X_2$-Y-Pro-[IGF-I] (SEQ ID NO: 31), wherein

[IGF-I] represents the amino acid sequence of IGF-I and
Met denotes methionine,
$X_1$ is a bond, serine or asparagine,
His is histidine,
n is a number from 0 to 6,
$X_2$ is a linker peptide, selected from the group of peptides SEQ ID NO: 6-10,
Pro is proline, and
Y is selected from the group consisting of Pro, Pro-Ala, Pro-Gly, Pro-Thr, Ala-Pro, Gly-Pro, Thr-Pro, Arg-Pro, or Pro-Arg-Pro.

Preferably the propeptide is shown by the formula Met-$X_1$-His$_n$-$X_2$-Y-Pro- (SEQ ID NO: 29), wherein Met denotes methionine
$X_1$ is a bond, serine or asparagine
His is histidine,
n is a number from 0 to 6,
$X_2$ is a linker peptide, selected from the group, consisting of peptides SEQ ID NO: 6-10,
Pro is proline, and
Y is selected from the group consisting of Pro, Pro-Ala, Pro-Gly, Pro-Thr, Ala-Pro, Gly-Pro, Thr-Pro, Arg-Pro, or Pro-Arg-Pro.

The propeptide is C-terminally linked to the N-terminus of IGF-I. The propeptide preferably has a length of up to 30 amino acids. Preferably X1 is a bond. Preferably n is 0 or 6. Preferably X2 is peptide SEQ ID NO:7. Preferably Y is Pro-Arg-Pro.

The invention further comprises pharmaceutical compositions containing an IGF-I according to the invention, preferably together with a pharmaceutically acceptable carrier.

The invention further comprises methods for the production of pharmaceutical compositions containing an IGF-I according to the invention.

The invention further comprises the use of an IGF-I according to the invention for the preparation of a medicament for the treatment of AD.

The invention further comprises methods for the treatment of AD, characterized in that a pharmaceutically effective amount of amino-reactive IGF-I is administered to a patient in need of such treatment, preferably in one to two applications per week.

DETAILED DESCRIPTION OF THE INVENTION

It was surprisingly found that IgA protease, preferably IgA protease from *Neisseria gonorrhoae*, is capable of cleaving the amino acid sequence Y-Pro.!.Gly-Pro (SEQ ID NO: 30). Y is selected from the group consisting of Pro, Pro-Ala, Pro-Gly, Pro-Thr, Ala-Pro, Gly-Pro, Thr-Pro, Arg-Pro, or Pro-Arg-Pro. Preferably useful as cleavage site is Pro-Pro.!.Gly-Pro (SEQ ID NO: 15) or Pro-Arg-Pro-Pro.!.Gly-Pro (SEQ ID NO:11) (.!. : cleavage position). The IgA protease cleavage site for the process according to the present invention has the amino acid consensus sequence Y-Pro.!.Gly-Pro, whereby Gly-Pro are the first two amino acids of IGF-I. Y preferably represents an amino acid sequence which ends with the amino acid(s) Pro, Pro-Ala, Arg-Pro or Pro-Arg-Pro. Such Y amino acid sequences, especially Pro-Arg-Pro can be prolonged by a further Ala or Pro-Ala group, as e.g. in Ala-Pro-Arg-Pro (SEQ ID NO:12) or Pro-Ala-Pro-Arg-Pro (SEQ ID NO:13). Particularly preferred are the cleavage amino acid sequences Pro-Arg-Pro-Pro.!. Gly-Pro (SEQ ID NO:11), Pro-Ala-Pro-.!.Gly-Pro (SEQ ID NO:14), Pro-Pro-.!.Gly-Pro (SEQ ID NO:15), Ala-Pro-Arg-Pro-Pro.!.Gly-Pro (SEQ ID NO:16) or Pro-Ala-Pro-Arg-Pro-Pro.!.Gly-Pro (SEQ ID NO:17).

In accordance with the present invention the term "IgA protease" includes proteases which specifically cleave IgA and which are described, for example, in Kornfeld, S. J. and Plaut, A. G., Rev. Infekt. Dis. 3 (1981) 521-534 as e.g. IgA1 protease from *Neisseria gonorrhoea* (type 2). Recombinant IgA proteases such as those described in DE-A 36 22 221; Koomey, J. M., et al. Proc. Natl. Acad. Sci. USA 79 (1982) 7881-7885; Bricker, J., et al., Proc. Natl. Acad. Sci. USA 80 (1983) 2681-2685; Pohlner, J., Nature 325 (1987) 458-462; and Halter, R., et al., EMBO J. 3 (1984) 1595-1601 are also just as suitable. Preferably said IgA protease is IgA protease from *Neisseria gonorrhoae*. Preferably said IgA1 protease from *Neisseria gonorrhoea* (type 2) has the sequence SEQ ID NO:21.

Naturally-occurring IGF-I is a human protein consisting of 70 amino acids which is also named somatomedin C and defined by SwissProt No. P01343. Use, activity and production are mentioned in, e.g., le Bouc, Y., et al., FEBS Lett. 196 (1986) 108-112; de Pagter-Holthuizen, P., et al., FEBS Lett. 195 (1986) 179-184; Sandberg Nordqvist, A.C., et al., Brain Res. Mol. Brain Res. 12 (1992) 275-277; Steenbergh, P. H., et al., Biochem. Biophys. Res. Commun. 175 (1991) 507-514; Tanner, J. M., et al., Acta Endocrinol. (Copenh.) 84 (1977) 681-696; Uthne, K., et al., J. Clin. Endocrinol. Metab. 39 (1974) 548-554; EP 0 123 228; EP 0 128 733; U.S. Pat. No. 5,861,373; U.S. Pat. No. 5,714,460; EP 0 597 033; WO 02/32449; WO 93/02695.

IGF-I according to the invention is a polypeptide selected from the group consisting of: a polypeptide having the amino acid sequence of SEQ ID NO: 1, C-terminal truncated IGF-I, R36A, and R37A. Preferably said IGF-I is C-terminally linked to human Fc from IgG, preferably from IgG1 or IgG4.

C-terminal truncated IGF-I (deletion of 3-6 amino acids) is a polypeptide having the amino acid sequence of SEQ ID NO. 1 but with 3-6 amino acids deleted at the C-terminus.

R36A denotes a polypeptide having the amino acid sequence of SEQ ID NO. 1 but with arginine instead of alanine at amino acid position 36.

R37A denotes a polypeptide haying the amino acid sequence of SEQ ID NO. 1 but with arginine instead of alanine, at amino acid position 37.

The gene coding for a the fusion protein is preferably placed under the control of suitable (preferably inducible) expression signals so that fusion proteins can be produced according to the requirements. Suitable prokaryotic or eukaryotic (plant as well as animal) cells can be used as host cells for the production of protein fusions; cell-free systems are, however, also possible.

A preferred embodiment of the process according to the present invention is characterized in that a host cell is transformed with a recombinant DNA or a recombinant vector, in which the DNA or the vector contains at least one copy of a gene which codes for a fusion protein according to the invention and the transformed cell is cultured in a suitable medium, the gene coding for the fusion protein is made to express in the transformed cell, the fusion protein is cleaved with IgA protease and IGF-I is isolated.

The expression of the fusion protein according to the invention can, for example, be improved at the DNA level by fusion with fragments of lysine-free beta-galactosidase gene, i.e., Y contains a part of a lysine-free beta-galactosidase protein. Other alternatives for increasing the expression of the fusion protein are known to the expert. The purification and separation of the expression product can be facilitated by fusion with other polypeptides, in particular, with polypeptides or proteins that are highly charged (e.g. poly(Lys, Arg)) or which can bind to particular substances with high affinity (e.g. streptavidin) (see e.g. EP-A 0 089 626, EP-A 0 306 610). Especially preferred linker peptides are peptides SEQ ID NO: 6-10, preferably N-terminally preceded by SHHHHHH (SEQ ID NO:18, NHHHHHH (SEQ ID NO:19) or HHHHHH (SEQ ID NO:20).

The present invention also provides a (recombinant) nucleic acid which codes for a fusion protein according to the present invention and in which an IgA protease cleavage site is incorporated in the junction region between the propeptide and IGF-I.

A recombinant DNA according to the present invention can be obtained in a manner known to one skilled in the area of molecular biology. For this a vector which contains a DNA sequence coding for the amino acid sequence of IGF-I is usually cleaved with restriction endonuclease(s) in the region of the 5' end of this gene and religated with oligonucleotides which contain the desired sequence.

In addition, the invention also provides a recombinant vector which contains at least one copy of a recombinant DNA according to the present invention. Vectors which are suitable as a basis for protein expression in prokaryotic organisms are known to the expert. This vector is preferably one which allows a high expression of the recombinant DNA according to the present invention. The recombinant DNA on the vector is preferably under the control of an inducible expression signal (e.g. lambda, tac, lac or trp promoter).

The vector according to the present invention can be present extrachromosomally (e.g. plasmid) as well as integrated in the genome of the host organism (e.g. bacteriophage lambda). The vector according to the present invention is preferably a plasmid. Vectors which are suitable in each case for gene expression in a particular host organism are known to one skilled in the area of molecular biology. It can be a eukaryotic vector, but preferably a prokaryotic vector. Examples of suitable vectors for the expression of the DNA according to the present invention in prokaryotes are, for instance, commercially available pUC and pUR vectors.

The invention also provides a cell, preferably a prokaryotic cell, particularly preferably an *E. coli* cell, which is transformed with the recombinant DNA according to the present invention or/and with a recombinant vector according to the present invention.

When the fusion protein is expressed in prokaryotes, sparingly soluble aggregates (refractile bodies, inclusion bodies) are formed which are inactive. Therefore the fusion protein must be transformed into its active form. Using procedures which are familiar to those skilled in the art (cf. e.g. EP-A 0 219 874, EP A 0 114 506, WO 84/03711) first a solubilization is carried out by addition of denaturing agents which is followed by renaturation and, if desired, further purification steps.

The conditions required for the treatment of an IGF-I fusion protein to be cleaved with IgA proteases are not critical. In this process it is, however, preferred that the ratio by weight of IGF-I fusion protein to IgA protease is 1:1 to 100:1. The reaction preferably takes place in a buffered aqueous solution of pH 6.5 to 8.5. The buffer concentration is preferably in the range between 50 and 500 mmol/l if desired, with addition of 0-100 mmol/l sodium chloride. The cleavage is preferably carried out at room temperature for at least 60 min up to 5 days, preferably between 24-72 h.

After solubilization, renaturation and cleavage with IgA protease the cleavage product obtained in this way is preferably purified by means of hydrophobic interaction chromatography, ion exchange chromatography and/or fractionation by size. The IGF-I produced in this way is free of methionine in position −1.

Pharmaceutical Formulations

IGF-I's can be administered as a mixture, or different species separated by e. g. hydrophobic interaction chromatography, ion exchange chromatography or size exclusion chromatography. The compounds of the present invention can be formulated according to methods for the preparation of pharmaceutical compositions, which methods are known to the person skilled in the art. For the production of such compositions, an IGF-I according to the invention is combined in a mixture with a pharmaceutically acceptable carrier, preferably by dialysis or diafiltration against an aqueous solution containing the desired ingredients of the pharmaceutical compositions. Such acceptable carriers are described, for example, in Remington's Pharmaceutical Sciences, 18$^{th}$ edition, 1990, Mack Publishing Company, edited by Oslo et al. (e.g. pp. 1435-1712). Typical compositions contain an effective amount of the substance according to the invention, for example from about 0.1 to 100 mg/ml, together with a suitable amount of a carrier. The compositions may be administered parenterally. The IGF-I according to the invention is administered preferably via intraperitoneal, subcutaneous, intravenous, or intranasal application.

The pharmaceutical formulations according to the invention can be prepared according to known methods in the art. Usually, solutions of IGF-I are dialyzed or diafiltrated against the buffer intended to be used in the pharmaceutical composition and the desired final protein concentration is adjusted by concentration or dilution.

The following examples and sequences are provided to aid the understanding of the present invention, the true scope of which is set forth in the appended claims. It is understood that modifications can be made in the procedures set forth without departing from the spirit of the invention. Names of the amino acids are abbreviated using either the one letter code (e.g. R) or the three letter code (e.g. Arg). R36A means an IGF-I mutant in which amino acid arginine36 is replaced by alanine.

Sequence Listing

SEQ ID NO: 1 amino acid sequence of human IGF-I (amino acids 49-118 from SwissProt P01343).

SEQ ID NO: 2 amino acid sequence of a preferred propeptide

SEQ ID NO: 3 amino acid sequence of a preferred propeptide

SEQ ID NO: 4 amino acid sequence of a preferred propeptide

SEQ ID NO: 5 amino acid sequence of a preferred propeptide

SEQ ID NO: 6-10 linker

SEQ ID NO: 11-17 cleavage sequences

SEQ ID NO: 18-20 others

SEQ ID NO: 21 amino acid sequence of an IgA1 protease from *Neisseria gonorrhoea* (type 2)

EXAMPLES

Example 1

The expression vector and the *E. coli* strain useful are described in EP 0 972 838. From an *E. coli* clone, expressing fusion protein are grown on selective agar plate, one inoculating loop is transferred to (100 ml) selective medium and cultivated for 13 h at 37° C. to an optical density (578 nm) of 2-4. This culture is stored on ice for the next 6 hours prior to the automated inoculation of the main culture which is performed at 37° C. The expression of IGF-I mutant is initiated at an optical density (578 nm) of 50 with the addition of 1.0 mM IPTG. The overall fermentation lasts up to 16 hours. The amount of protein is determined densitometrically by comparing the volumetric intensity of the protein band of the product with the band of an IGF standard on a SDS-PAGE gel. The culture broth is harvested by centrifugation.

To obtain purified inclusion body (IB) material, the harvested biomass out of standard fermentation is treated with the following procedure: 0.3 g/100 g bio dry weight Lysozyme and 5 U/1 g bio dry weight Benzonase are incubated for 20 min and homogenized. 30 U/1 g bio dry weight Benzonase is added and incubated for 60 min. at 37 ° C. 0.5 L Brij-buffer/liter is added and incubated for 30 min. at RT. After centrifugation the pellet is resuspended in 300 ml Tris-EDTA-Puffer/100 g bio wet weight (purified IB wet weight), incubated for 30 min. at RT and centrifugated. 1 g IBs/liter are solubilized at room temperature in 6.8 M guanidine-HCl, 0.1 M TrisHCl, 0.1 M DTT, pH 8.5 overnight. The turbid solution is dialyzed at 4° C. against 6.8 M guanidine-HCl, 0.1 M TrisHCl, pH 8.0. After dialysis insoluble components were removed by centrifugation. Folding is performed by 50-fold dilution of the pro-IGF-I solution into 0.8 M arginine, 0.1 M TrisHCl, 0.1 M guanidine-HCl, 1 mM GSH, 1 mM GSSH, pH 8.5 at room temperature. After two hours the solution is supplemented with 2 M sodium chloride, filtered and applied at a flow rate of 10 ml/min to a HIC column (Butyl Sepharose 4 Fast Flow; GE, Amersham Biosciences), which is equilibrated at room temperature with buffer containing 2 M NaCl, 0.8 M arginine, 0.1 M TrisHCl, 0.1 M guanidine-HCl, pH 8.5. The column is washed with equilibration buffer till baseline is achieved and then eluted with ten column volumes of a linear gradient starting with equilibration buffer and ending with buffer containing 0.1 M TrisHCl, 5% ethylene glycol, pH 8.5. Eluted fractions are analyzed by reversed phase high performance chromatography (rpHPLC). Fractions that contain protein with correctly formed SS-bridges were pooled. The reaction mix is supplemented with IgA1 protease from *Neisseria gonorrhoea* (type 2) (w/w ratio 1:50) and incubated over night at room temperature (see FIG. 2). The reaction mix is diluted 1:2 with 50 mM acetic acid pH 4.5 and then applied to a cation IEC column (MacroCap SP support; GE, Amersham Biosciences, Uppsala, Sweden), equilibrated with 50 mM acetic acid or applied to a SEC Superdex™ 200 (General Electric). The column is washed till baseline is reached and then eluted with 20 column volumes of a linear gradient starting with 50 mM acetic acid and ending with 50 mM acetic acid supplemented with 1 M sodium chloride. Eluted fractions were analyzed by SDS-PAGE. Fractions containing a single band with IGF-I molecular size are pooled as IGF-I. Identity of IGF-I is verified by analytical size exclusion chromatography (SEC) with static light scattering detection, MS analysis of tryptic digests, MS analysis of Asp-N digests and analytical cation IEC or SEC.

The invention claimed is:

1. A method for the production of IGF-I, said method comprising:
   a) cultivating a prokaryotic host cell comprising an expression vector containing a nucleic acid encoding a fusion protein comprising said IGF-I N-terminally linked to the C-terminus of a propeptide, whereby said propeptide ends C-terminally with amino acids -Y-Pro, wherein Y is selected from the group consisting of Pro, Pro-Ala, Arg-Pro, and Pro-Arg-Pro, and
   b) recovering and cleaving said fusion protein with IgA protease to recover said IGF-I.

2. The method of claim 1, wherein said IGF-I is selected from the group consisting of: IGF-I (SEQ ID NO:1), an IGF-I SEQ ID NO: 1, in which at the C-terminus 3-6 amino acids are deleted, IGF-I of SEQ ID NO. 1, in which at amino acid position 36 arginine is substituted by alanine, and IGF-I of SEQ ID NO. 1, in which at amino acid position 37 arginine is substituted by alanine.

3. The method of claim 1, wherein said IGF-I is C-terminally linked to human Fc from IgG.

4. The method of claim 1, wherein said propeptide has the following amino acid sequence:
Met-$X_1$-His$_n$-$X_2$-Y-Pro-, wherein
   Met denotes methionine,
   $X_1$ is a bond, serine or asparagine,
   His is histidine,
   n is a number from 0 to 6,
   $X_2$ is a linker peptide, selected from the group consisting of peptides SEQ ID NO: 6-10,
   Pro is proline, and
   Y is selected from the group consisting of Pro, Pro-Ala, Arg-Pro, and Pro-Arg-Pro.

* * * * *

UNITED STATES PATENT AND TRADEMARK OFFICE
CERTIFICATE OF CORRECTION

| | | |
|---|---|---|
| PATENT NO. | : 8,552,158 B2 | Page 1 of 1 |
| APPLICATION NO. | : 12/438154 | |
| DATED | : October 8, 2013 | |
| INVENTOR(S) | : Stephan Fischer et al. | |

It is certified that error appears in the above-identified patent and that said Letters Patent is hereby corrected as shown below:

Title Page, Item (75) Inventors:

Change "Stephan Fischer, Polling (DE)" to -- Stephan Fischer, Weilheim (DE) --

Change "Christian Schantz, Munich (DE)" to -- Christian Schantz, Penzberg (DE) --

Signed and Sealed this
Twenty-eighth Day of January, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,552,158 B2                                    Page 1 of 1
APPLICATION NO. : 12/438154
DATED            : October 8, 2013
INVENTOR(S)      : Fischer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 602 days.

Signed and Sealed this
Fifteenth Day of September, 2015

Michelle K. Lee
*Director of the United States Patent and Trademark Office*

SEQUENCE LISTING

<160> NUMBER OF SEQ ID NOS: 31

<210> SEQ ID NO 1
<211> LENGTH: 70
<212> TYPE: PRT
<213> ORGANISM: Homo sapiens

<400> SEQUENCE: 1

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

```
Phe Arg Ser Cys Asp Leu Arg Arg Leu Glu Met Tyr Cys Ala Pro Leu
 50                  55                  60

Lys Pro Ala Lys Ser Ala
 65                  70

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Met His His His His His His Arg Ala Arg Arg Phe Arg Arg His Pro
 1               5                  10                  15

Arg Pro Pro

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Met Ser His His His His His His Asn His Asn Arg Glu His Pro Arg
 1               5                  10                  15

Pro Pro

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met Asn His His His His His His Ile Glu Gly Arg His Pro Arg Pro
 1               5                  10                  15

Pro

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Met Asn His His His His His His Thr Glu Phe Glu Asn Ile Glu His
 1               5                  10                  15

Pro Arg Pro Pro
             20

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 6

Lys Ala Lys Arg Phe Lys Lys His
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ala Arg Arg Phe Arg Arg His
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asn Thr Glu His Asn Arg Glu His
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Glu Gly Arg His
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Glu Phe Glu Asn Ile Glu His
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Pro Arg Pro Pro Gly Pro
1               5

<210> SEQ ID NO 12
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 12

Ala Pro Arg Pro
1

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Pro Ala Pro Arg Pro
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Pro Ala Pro Gly Pro
1               5

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Pro Pro Gly Pro
1

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Pro Arg Pro Pro Gly Pro
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Pro Ala Pro Arg Pro Pro Gly Pro
1               5
```

```
<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser His His His His His His
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asn His His His His His His
1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

His His His His His His
1               5

<210> SEQ ID NO 21
<211> LENGTH: 960
<212> TYPE: PRT
<213> ORGANISM: Neisseria gonorrhoea

<400> SEQUENCE: 21

Met Ala Leu Val Arg Asp Asp Val Asp Tyr Gln Ile Phe Arg Asp Phe
1               5                   10                  15

Ala Glu Asn Lys Gly Lys Phe Phe Val Gly Ala Thr Asp Leu Ser Val
                20                  25                  30

Lys Asn Lys Arg Gly Gln Asn Ile Gly Asn Ala Leu Ser Asn Val Pro
            35                  40                  45

Met Ile Asp Phe Ser Val Ala Asp Val Asn Lys Arg Ile Ala Thr Val
        50                  55                  60

Val Asp Pro Gln Tyr Ala Val Ser Val Lys His Ala Lys Ala Glu Val
65                  70                  75                  80

His Thr Phe Tyr Tyr Gly Gln Tyr Asn Gly His Asn Asp Val Ala Asp
                85                  90                  95

Lys Glu Asn Glu Tyr Arg Val Val Glu Gln Asn Asn Tyr Glu Pro His
                100                 105                 110

Lys Ala Trp Gly Ala Ser Asn Leu Gly Arg Leu Glu Asp Tyr Asn Met
            115                 120                 125

Ala Arg Phe Asn Lys Phe Val Thr Glu Val Ala Pro Ile Ala Pro Thr
        130                 135                 140

Asp Ala Gly Gly Gly Leu Asp Thr Tyr Lys Asp Lys Asn Arg Phe Ser
145                 150                 155                 160
```

-continued

Ser Phe Val Arg Ile Gly Ala Gly Arg Gln Leu Val Tyr Glu Lys Gly
                165                 170                 175

Val Tyr His Gln Glu Gly Asn Glu Lys Gly Tyr Asp Leu Arg Asp Leu
            180                 185                 190

Ser Gln Ala Tyr Arg Tyr Ala Ile Ala Gly Thr Pro Tyr Lys Asp Ile
        195                 200                 205

Asn Ile Asp Gln Thr Met Asn Thr Glu Gly Leu Ile Gly Phe Gly Asn
    210                 215                 220

His Asn Lys Gln Tyr Ser Ala Glu Glu Leu Lys Gln Ala Leu Ser Gln
225                 230                 235                 240

Asp Ala Leu Thr Asn Tyr Gly Val Leu Gly Asp Ser Gly Ser Pro Leu
                245                 250                 255

Phe Ala Phe Asp Lys Gln Lys Asn Gln Trp Val Phe Leu Gly Thr Tyr
            260                 265                 270

Asp Tyr Trp Ala Gly Tyr Gly Lys Lys Ser Trp Gln Glu Trp Asn Ile
        275                 280                 285

Tyr Lys Lys Glu Phe Ala Asp Lys Ile Lys Gln His Asp Asn Ala Gly
    290                 295                 300

Thr Val Lys Gly Asn Gly Glu His His Trp Lys Thr Thr Gly Thr Asn
305                 310                 315                 320

Ser His Ile Gly Ser Thr Ala Val Arg Leu Ala Asn Asn Glu Gly Asp
                325                 330                 335

Ala Asn Asn Gly Gln Asn Val Thr Phe Glu Asp Asn Gly Thr Leu Val
            340                 345                 350

Leu Asn Gln Asn Ile Asn Gln Gly Ala Gly Leu Phe Phe Lys Gly
        355                 360                 365

Asp Tyr Thr Val Lys Gly Ala Asn Asn Asp Ile Thr Trp Leu Gly Ala
    370                 375                 380

Gly Ile Asp Val Ala Asp Gly Lys Lys Val Val Trp Gln Val Lys Asn
385                 390                 395                 400

Pro Asn Gly Asp Arg Leu Ala Lys Ile Gly Lys Gly Thr Leu Glu Ile
                405                 410                 415

Asn Gly Thr Gly Val Asn Gln Gly Gln Leu Lys Val Gly Asp Gly Thr
            420                 425                 430

Val Ile Leu Asn Gln Lys Ala Asp Ala Asp Lys Lys Val Gln Ala Phe
        435                 440                 445

Ser Gln Val Gly Ile Val Ser Gly Arg Gly Thr Leu Val Leu Asn Ser
    450                 455                 460

Ser Asn Gln Ile Asn Pro Asp Asn Leu Tyr Phe Gly Phe Arg Gly Gly
465                 470                 475                 480

Arg Leu Asp Ala Asn Gly Asn Asp Leu Thr Phe Glu His Ile Arg Asn
                485                 490                 495

Val Asp Glu Gly Ala Arg Ile Val Asn His Asn Thr Asp His Ala Ser
            500                 505                 510

Thr Ile Thr Leu Thr Gly Lys Ser Leu Ile Thr Asn Pro Asn Ser Leu
        515                 520                 525

Ser Val His Ser Ile Gln Asn Asp Tyr Asp Glu Asp Tyr Ser Tyr
    530                 535                 540

Tyr Tyr Arg Pro Arg Arg Pro Ile Pro Gln Gly Lys Asp Leu Tyr Tyr
545                 550                 555                 560

Lys Asn Tyr Arg Tyr Tyr Ala Leu Lys Ser Gly Gly Arg Leu Asn Ala
                565                 570                 575

Pro Met Pro Glu Asn Gly Val Ala Glu Asn Asn Asp Trp Ile Phe Met
            580                 585                 590

```
Gly Tyr Thr Gln Glu Glu Ala Arg Lys Asn Ala Met Asn His Lys Asn
            595                 600                 605

Asn Arg Arg Ile Gly Asp Phe Gly Gly Phe Phe Asp Glu Glu Asn Gly
610                 615                 620

Lys Gly His Asn Gly Ala Leu Asn Leu Asn Phe Asn Gly Lys Ser Ala
625                 630                 635                 640

Gln Asn Arg Phe Leu Leu Thr Gly Gly Ala Asn Leu Asn Gly Lys Ile
            645                 650                 655

Ser Val Thr Gln Gly Asn Val Leu Leu Ser Gly Arg Pro Thr Pro His
            660                 665                 670

Ala Arg Asp Phe Val Asn Lys Ser Ser Ala Arg Lys Asp Ala His Phe
            675                 680                 685

Ser Lys Asn Asn Glu Val Val Phe Glu Asp Asp Trp Ile Asn Arg Thr
690                 695                 700

Phe Lys Ala Ala Glu Ile Ala Val Asn Gln Ser Ala Ser Phe Ser Ser
705                 710                 715                 720

Gly Arg Asn Val Ser Asp Ile Thr Ala Asn Ile Thr Ala Thr Asp Asn
            725                 730                 735

Ala Lys Val Asn Leu Gly Tyr Lys Asn Gly Asp Glu Val Cys Val Arg
            740                 745                 750

Ser Asp Tyr Thr Gly Tyr Val Thr Cys Asn Thr Gly Asn Leu Ser Asp
            755                 760                 765

Lys Ala Leu Asn Ser Phe Asp Ala Thr Arg Ile Asn Gly Asn Val Asn
770                 775                 780

Leu Asn Gln Asn Ala Ala Leu Val Leu Gly Lys Ala Ala Leu Trp Gly
785                 790                 795                 800

Lys Ile Gln Gly Gln Gly Asn Ser Arg Val Ser Leu Asn Gln His Ser
            805                 810                 815

Lys Trp His Leu Thr Gly Asp Ser Gln Val His Asn Leu Ser Leu Ala
            820                 825                 830

Asp Ser His Ile His Leu Asn Asn Ala Ser Asp Ala Gln Ser Ala Asn
            835                 840                 845

Lys Tyr His Thr Ile Lys Ile Asn His Leu Ser Gly Asn Gly His Phe
            850                 855                 860

His Tyr Leu Thr Asp Leu Ala Lys Asn Leu Gly Asp Lys Val Leu Val
865                 870                 875                 880

Lys Glu Ser Ala Ser Gly His Tyr Gln Leu His Val Gln Asn Lys Thr
            885                 890                 895

Gly Glu Pro Asn Gln Glu Gly Leu Asp Leu Phe Asp Ala Ser Ser Val
            900                 905                 910

Gln Asp Arg Ser Arg Leu Phe Val Ser Leu Ala Asn His Tyr Val Asp
            915                 920                 925

Leu Gly Ala Leu Arg Tyr Thr Ile Lys Thr Glu Asn Gly Ile Thr Arg
            930                 935                 940

Leu Tyr Asn Pro Tyr Ala Gly Asn Arg Arg Pro Val Lys Pro Ala Pro
945                 950                 955                 960
```

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 22

Lys Pro Ala Pro Ser Pro
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Val Ala Pro Pro Ser Pro
1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Pro Arg Pro Pro Ala Pro
1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Pro Arg Pro Pro Ser Pro
1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Pro Arg Pro Pro Thr Pro
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Pro Pro Thr Pro Ser Pro
1               5

<210> SEQ ID NO 28
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 28

Ser Thr Pro Pro Thr Pro
1               5

<210> SEQ ID NO 29
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser, Asp or not present
<220> FEATURE:
<221> NAME/KEY: MOD_RES
<222> LOCATION: (3)..(8)
<223> OTHER INFORMATION: This region may encompass 0-6 His residues
<220> FEATURE:
<221> NAME/KEY: MOD_RES
<222> LOCATION: (9)..(9)
<223> OTHER INFORMATION: Lys, Arg, Asn, Ile or Thr
<220> FEATURE:
<221> NAME/KEY: MOD_RES
<222> LOCATION: (10)..(10)
<223> OTHER INFORMATION: Ala, Thr or Glu
<220> FEATURE:
<221> NAME/KEY: MOD_RES
<222> LOCATION: (11)..(11)
<223> OTHER INFORMATION: Lys, Arg, Glu, Gly or Phe
<220> FEATURE:
<221> NAME/KEY: MOD_RES
<222> LOCATION: (12)..(12)
<223> OTHER INFORMATION: Arg, His or Glu
<220> FEATURE:
<221> NAME/KEY: MOD_RES
<222> LOCATION: (13)..(13)
<223> OTHER INFORMATION: Phe, Asn or His
<220> FEATURE:
<221> NAME/KEY: MOD_RES
<222> LOCATION: (14)..(14)
<223> OTHER INFORMATION: Lys, Arg, Ile or not present
<220> FEATURE:
<221> NAME/KEY: MOD_RES
<222> LOCATION: (15)..(15)
<223> OTHER INFORMATION: Lys, Arg, Glu or not present
<220> FEATURE:
<221> NAME/KEY: MOD_RES
<222> LOCATION: (16)..(16)
<223> OTHER INFORMATION: His or not present
<220> FEATURE:
<221> NAME/KEY: MOD_RES
<222> LOCATION: (19)..(19)
<223> OTHER INFORMATION: Ala, Gly, Thr, Pro, Arg or not present
<220> FEATURE:
<221> NAME/KEY: MOD_RES
<222> LOCATION: (20)..(20)
<223> OTHER INFORMATION: Pro or not present
<220> FEATURE:
<223> OTHER INFORMATION: see specification as filed for detailed
      description of substitutions and preferred embodiments

<400> SEQUENCE: 29

Met Xaa His His His His His His Xaa Xaa Xaa Xaa Xaa Xaa Xaa Xaa
1               5                   10                  15

Pro Pro Xaa Xaa
            20
```

```
<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ala, Gly, Thr, Pro, Arg or not present
<220> FEATURE:
<221> NAME/KEY: MOD_RES
<222> LOCATION: (4)..(4)
<223> OTHER INFORMATION: Pro or not present
<220> FEATURE:
<223> OTHER INFORMATION: see specification as filed for detailed
      description of substitutions and preferred embodiments

<400> SEQUENCE: 30

Pro Pro Xaa Xaa Pro Gly Pro
1               5

<210> SEQ ID NO 31
<211> LENGTH: 90
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A bond, Ser or Asp
<220> FEATURE:
<221> NAME/KEY: MOD_RES
<222> LOCATION: (3)..(8)
<223> OTHER INFORMATION: This region may encompass 0-6 His residues
<220> FEATURE:
<221> NAME/KEY: MOD_RES
<222> LOCATION: (9)..(9)
<223> OTHER INFORMATION: Lys, Arg, Asn, Ile or Thr
<220> FEATURE:
<221> NAME/KEY: MOD_RES
<222> LOCATION: (10)..(10)
<223> OTHER INFORMATION: Ala, Thr or Glu
<220> FEATURE:
<221> NAME/KEY: MOD_RES
<222> LOCATION: (11)..(11)
<223> OTHER INFORMATION: Lys, Arg, Glu, Gly or Phe
<220> FEATURE:
<221> NAME/KEY: MOD_RES
<222> LOCATION: (12)..(12)
<223> OTHER INFORMATION: Arg, His or Glu
<220> FEATURE:
<221> NAME/KEY: MOD_RES
<222> LOCATION: (13)..(13)
<223> OTHER INFORMATION: Phe, Asn or His
<220> FEATURE:
<221> NAME/KEY: MOD_RES
<222> LOCATION: (14)..(14)
<223> OTHER INFORMATION: Lys, Arg, Ile or not present
<220> FEATURE:
<221> NAME/KEY: MOD_RES
<222> LOCATION: (15)..(15)
<223> OTHER INFORMATION: Lys, Arg, Glu or not present
<220> FEATURE:
<221> NAME/KEY: MOD_RES
<222> LOCATION: (16)..(16)
<223> OTHER INFORMATION: His or not present
<220> FEATURE:
<221> NAME/KEY: MOD_RES
<222> LOCATION: (19)..(19)
<223> OTHER INFORMATION: Ala, Gly, Thr, Pro, Arg or not present
<220> FEATURE:
<221> NAME/KEY: MOD_RES
<222> LOCATION: (20)..(20)
<223> OTHER INFORMATION: Pro or not present
```

```
<220> FEATURE:
<223> OTHER INFORMATION: see specification as filed for detailed
      description of substitutions and preferred embodiments

<400> SEQUENCE: 31

Met Xaa His His His His His Xaa Xaa Xaa Xaa Xaa Xaa Xaa Xaa
1               5                   10                  15

Pro Pro Xaa Xaa Gly Pro Glu Thr Leu Cys Gly Ala Glu Leu Val Asp
            20                  25                  30

Ala Leu Gln Phe Val Cys Gly Asp Arg Gly Phe Tyr Phe Asn Lys Pro
        35                  40                  45

Thr Gly Tyr Gly Ser Ser Ser Arg Arg Ala Pro Gln Thr Gly Ile Val
    50                  55                  60

Asp Glu Cys Cys Phe Arg Ser Cys Asp Leu Arg Arg Leu Glu Met Tyr
65                  70                  75                  80

Cys Ala Pro Leu Lys Pro Ala Lys Ser Ala
                85              90
```